US00PP29805P2

(12) United States Plant Patent
Smith

(10) Patent No.: US PP29,805 P2
(45) Date of Patent: Nov. 6, 2018

(54) ***CHRYSANTHEMUM* PLANT NAMED 'CIFZ0047'**

(50) Latin Name: *Chrysanthemum x morifolium*
Varietal Denomination: CIFZ0047

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 72 days.

(21) Appl. No.: 15/530,546

(22) Filed: Jan. 26, 2017

(51) Int. Cl.
*A01H 5/02* (2018.01)

(52) U.S. Cl.
USPC ..... Plt./293

(58) Field of Classification Search
USPC ..... Plt./263.1, 284, 286, 287, 293
See application file for complete search history.

(56) References Cited

U.S. PATENT DOCUMENTS

PP26,321 P2 * 1/2016 Smith ..... A01H 6/1424 Plt./292

OTHER PUBLICATIONS

Dowrick and Bayoumi. 1966. The induction of mutations in *Chrysanthemum* using x- and gamma radiation. Euphytica 15: 204-210.*

* cited by examiner

*Primary Examiner* — Susan McCormick Ewoldt
*Assistant Examiner* — Karen M Redden
(74) *Attorney, Agent, or Firm* — Dale Skalla

(57) ABSTRACT

A new garden type *Chrysanthemum* plant named 'CIFZ0047' particularly distinguished by the medium size red-purple decorative flower, a medium-large size plant with round mounded plant habit and a natural season response in mid-September.

1 Drawing Sheet

Latin name of the genus and species of the plant claimed: *Chrysanthemum* x *morifolium*.

Varietal denomination: 'CIFZ0047'.

BACKGROUND OF THE NEW PLANT

The present invention comprises a new *Chrysanthemum*, botanically known as *Chrysanthemum* x *morifolium*, and hereinafter referred to by the variety name 'CIFZ0047'.

'CIFZ0047' is a product of a planned breeding program. The new cultivar has medium size red-purple decorative flower, a medium-large size plant with round mounded plant habit and a natural season response in mid-September.

'CIFZ0047' originated from a mutation: Stock x-rayed at 1750 RAD in October of 2013. Single cutting sport from the stock.

The female parent was 'Patty Purple', U.S. Plant Pat. No. 26,321.

| Compared to the female parent, 'CIFZ0047' has: |
|---|
| 1) Similar flower type and size but more red/less purple than 'Patty Purple' |
| 2) Blackcloth and natural season response is one or two days faster than 'Patty Purple' |
| 3) Similar plant habit with slightly smaller overal plant size than 'Patty Purple' |

No male parent.

The first act of asexual reproduction of 'CIFZ0047' was accomplished when vegetative cuttings were propagated from the initial selection, this initial selection took place in Apr. 16, 2014 in Gilroy, Calif.

BRIEF SUMMARY OF INVENTION

Horticultural examination of plants grown from cuttings of the plant initiated in May 2014 in Gilroy, Calif., and continuing thereafter, has demonstrated that the combination of characteristics as herein disclosed for 'CIFZ0047' are firmly fixed and are retained through successive generations of asexual reproduction.

'CIFZ0047' has not been observed under all possible environmental conditions. The phenotype may vary significantly with variations in environment such as temperature, light intensity and day length.

'CIFZ0047' has not been made publicly available prior to the effective filing date of this application, notwithstanding any disclosure that may have been made less than one year prior to the effective filing date of this application by the inventor or another who obtained 'CIFZ0047' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0047' with colors being as true as possible with an illustration of this type.

Figure 1:
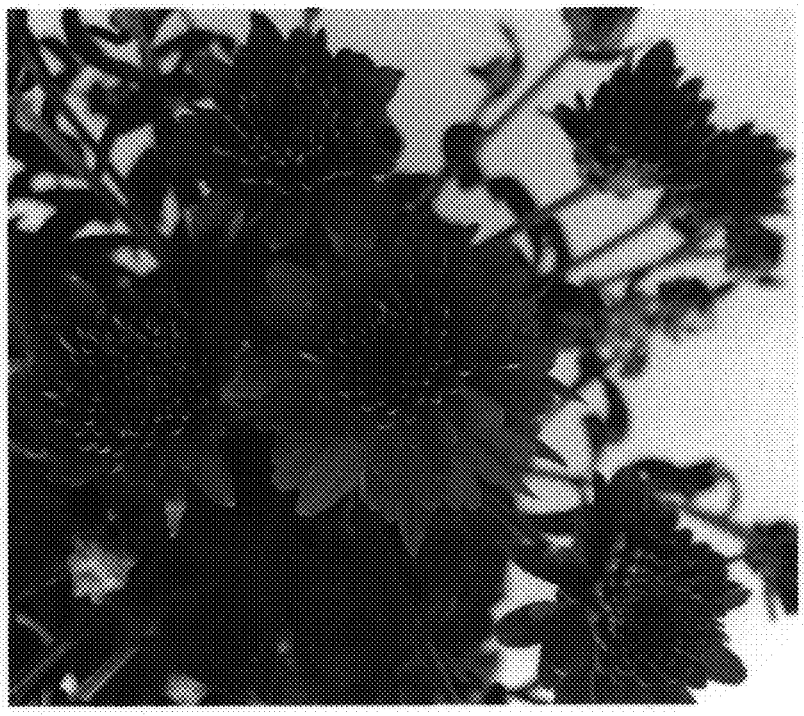
Figure 2:
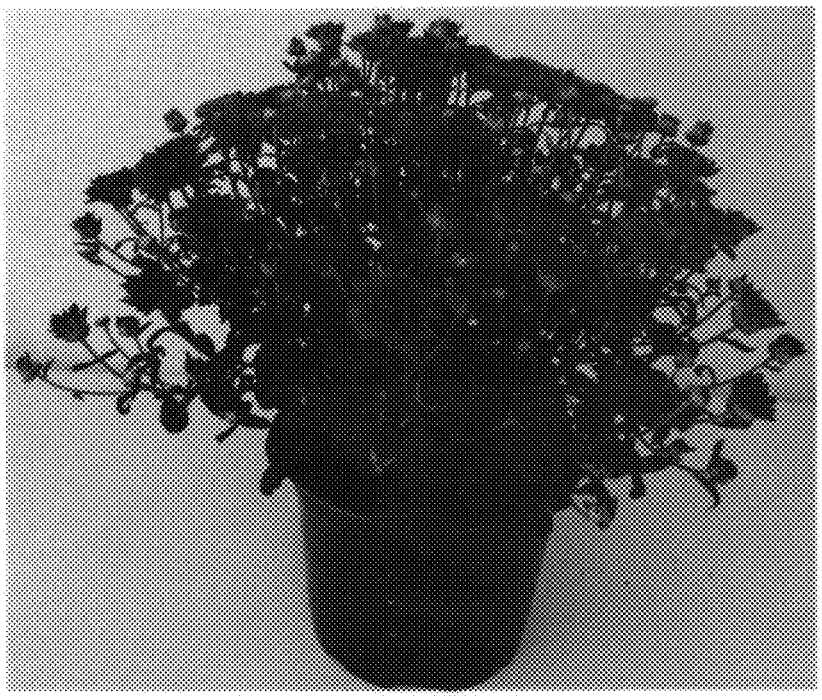

The photographic drawing shows in FIG. 1 a close view of flower of the new variety and in FIG. 2 a flowering plant from an indoor trial.

The aforementioned photographs: FIG. 1, as well as FIG. 2, were taken in August 2016 both showing a plant from the same blackcloth indoor trial in Gilroy, Calif. These plants were about 9 weeks of age. One rooted cutting per pot had been planted in a 6 inch pot in week 24, not pinched. Shortday blackcloth treatment was applied from week 25 on. Plants started flowering in August.

DETAILED BOTANICAL DESCRIPTION

The measurements were taken in Gilroy, Calif. in August 2016 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0047' AND TWO MOST SIMILAR VARIETIES:

| | 'CIFZ0047' | 'Synhes Hored', U.S. Plant Pat. No. 23,519 |
|---|---|---|
| Flowering response (blackcloth): | Similar | Similar |
| Flowering response (natural): | Similar | Similar |
| Uniformity of flowering: | Uniform | Less uniform |
| Flower color: | Red-purple | Red-scarlet |
| Flower size: | Bit smaller | Bit bigger |
| Plant habit or size: | Rounder habit | More upright habit |

| | 'CIFZ0047' | 'Granata Red', U.S. Plant Pat. No. 23,135 |
|---|---|---|
| Flowering response (blackcloth): | Similar except in the south where this variety can be a half a week slower | Similar except in the south where this variety can be a half a week faster |
| Flower color: | Red-purple | Red-scarlet |
| Plant habit or size: | Smaller plant | Bigger plant |

Plant:

*Form, growth and habit.*—Herbaceous garden-type, stems upright and outwardly spreading, freely branching, strong and moderately vigorous growth habit.

*Plant height (above soil).*—14-17 cm.

*Plant height (inflorescence included).*—17-20 cm.

*Plant width.*—29-31 cm.

Roots:

*Number of days to initiate roots.*—About 4 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature leaf, color upper surface.*—RHS 136A.

*Immature leaf, color lower surface.*—RHS 137A.

*Mature leaf, color, upper surface.*—Between RHS 139A and RHS 136A.

*Mature leaf, color lower surface.*—RHS 137A.

*Length.*—3.7-5.0 cm.

*Width.*—3.2-3.7 cm.

*Shape.*—Ovate.

*Base shape.*—Attenuate.

*Apex shape.*—Acute.

*Margin.*—3 main lobes, irregularly serrated.

*Texture, upper surface.*—Bifid hairs.

*Texture, lower surface.*—Bifid hairs.

*Color of veins, upper surface.*—RHS 141A.

*Color of veins, lower surface.*—RHS 137B.

*Pattern of veining.*—Palmate.

*Petiole color.*—RHS 137C.

*Petiole length.*—2.0-2.8 cm.

*Diameter.*—0.15-0.2 cm.

*Texture.*—Covered with bifid hairs.

Stem:

*Quantity of main branches per plant.*—5-7.

*Color of stem.*—RHS 137B.

*Length of stem.*—14-17 cm.

*Diameter.*—0.3-0.5 cm.

*Length of internodes.*—0.5-1.0 cm.

*Texture.*—Bifid hairs.

*Color of peduncle.*—RHS 137C.

*Length of peduncle.*—4.3-4.9 cm.

*Peduncle diameter.*—0.15 cm.

*Texture.*—Bifid hairs.

Inflorescence:

*Type.*—Compositae, solitary, decorative-type inflorescences borne terminally above foliage, ray florets arranged on a capitulum.

*Quantity of short days to flowering (response time).*—Approximately 6 weeks.

*Natural season flowering.*—Mid-September.

*Quantity of inflorescences per plant.*—60-80, with many small buds developing.

*Lastingness of individual blooms on the plant.*—About 5.5 weeks from first color.

*Fragrance.*—Slightly spicy.

Bud (when showing color):

*Color.*—RHS 187B.

*Length.*—1.0-1.3 cm.

*Width.*—0.9-1.1 cm.

*Shape.*—Oblate.

Immature inflorescence:

*Diameter.*—1.8-2.5 cm.

*Color of ray florets, upper surface.*—RHS 185A.

*Color of ray florets, lower surface.*—RHS 185A, overlain with RHS 12D.

Mature inflorescence:

*Diameter.*—3.4-3.9 cm.

*Depth.*—1.2-1.4 cm.

*Total diameter of disc.*—Very small; not visible as covered by the many rays.

*Receptacle color.*—RHS 145B.

*Receptacle height.*—0.2 cm.

*Receptacle diameter.*—0.3 cm.

Ray florets:

*Average quantity of florets.*—Between 150 and 170 in many whorls.

*Color of florets, upper surface (abaxial).*—RHS 60A.

*Color inner surface (adaxial).*—RHS 60A overlain with RHS 12D.

*Length.*—0.7-2.0 cm.

*Width/diameter.*—0.4-0.6 cm.

*Shape.*—Oblong to elliptical.

*Apex shape.*—Most often emarginated or praemorse.

*Base shape*.—Attenuate.
*Margin*.—Entire.
*Texture, upper surface*.—Smooth.
*Lower surface*.—Smooth.

Disc florets: None present.

Phyllaries:
*Quantity*.—Approximately 20.
*Color, upper surface*.—RHS 137C.
*Color, lower surface*.—RHS 137B.
*Length*.—0.6-0.7 cm.
*Width*.—0.15-2.0 cm.
*Shape*.—Lanceolate.
*Apex shape*.—Acute.
*Base*.—Fused.
*Margins*.—Entire, some with papery edges.
*Texture, upper surface*.—Glabrous.
*Texture, lower surface*.—Bifid hairs.

Reproductive organs:
*Pistil*.—One.
*Length*.—0.5-0.6 cm.
*Style color*.—RHS 1C.
*Style length*.—0.35-0.4 cm.
*Stigma color*.—RHS 7D.
*Stigma shape*.—Bi-lobed.
*Ovary color*.—RHS 145C.
*Ovary length*.—0.15 cm.
*Ovary width*.—0.1 cm.

Androecium:
*Stamens*.—None, as they are usually present in disc florets only, which are not developed.
*Fertility/seed set*.—Has not been determined to date.
*Disease/pest resistance*.—Has not been determined to date.

What is claimed is:

1. A new and distinct variety of *Chrysanthemum* plant named 'CIFZ0047' substantially as illustrated and described herein.

* * * * *